United States Patent
Mao et al.

(10) Patent No.: US 6,844,323 B2
(45) Date of Patent: Jan. 18, 2005

(54) POLYPEPTIDE-CALCITONIN 11 AND THE POLYNUCLEOTIDE ENCODING IT

(75) Inventors: Yumin Mao, Shanghai (CN); Yi Xie, Shanghai (CN)

(73) Assignee: BioWindow Gene Development Inc., Shanghai (CN)

( * ) Notice: Subject to any disclaimer, the term of this patent is extended or adjusted under 35 U.S.C. 154(b) by 407 days.

(21) Appl. No.: 10/168,626

(22) PCT Filed: Dec. 18, 2000

(86) PCT No.: PCT/CN00/00605

§ 371 (c)(1),
(2), (4) Date: Jun. 24, 2002

(87) PCT Pub. No.: WO01/46253

PCT Pub. Date: Jun. 28, 2001

(65) Prior Publication Data

US 2004/0038873 A1 Feb. 26, 2004

(30) Foreign Application Priority Data

Dec. 22, 1999 (CN) ........................................ 99125679 A

(51) Int. Cl.[7] ........................ A61K 38/17; C07K 14/47

(52) U.S. Cl. .......................................... 514/12; 530/324

(58) Field of Search .............................. 514/12; 530/324

(56) References Cited

PUBLICATIONS

DNA Res. 6(1), 63–70 (1999), Nagase T., et al., *Prediction of the sequences of unidentified human genes. XIII. The complete sequences of 100 new cDNA clones from brain which code for large proteins in vitro.*

Genome Res. 9(3), 242–250 (1999), Reboul, J., Et al., *Comparative genomic analysis of the interferon/Interleukin–10 receptor gene cluster.*

Primary Examiner—Robert A. Wax
(74) Attorney, Agent, or Firm—Crowell & Moring LLP

(57) ABSTRACT

The present invention discloses a new polypeptide-calcitonin 11, the polynucleotide encoding it and a method producing the polypeptide by recombinant DNA technology. The present invention further discloses a method using the polypeptide to treat various disorders, e.g. malignant neoplasm, hematopathy, HIV infection and immunological disease and various inflammation etc. The present invention also discloses agonists of the polypeptide and their therapeutic uses. The present invention further discloses the use of the polynucleotide encoding the new calcitonin 11.

4 Claims, 1 Drawing Sheet

```
S   12 QGELESQRLATAVMIHLQHQAHCYLHKSRIYLNWRKQKMHSSVVTQWSLL 61
          ..|:| .: |.:     ::.:.    .|      |. :: :||: .|: |
P    3 EEEEEQEPEGSS....LDRPV....SK.......RSCNTATCVTQRLAQL 37

.       _   .          .
S   62 QKEFTGVHSVCQGAGFLSLVFITLFHPTCVGSAT 95
          ..:              ..   | || |||.|
P   38 LNRSGG.............VVKQTFPPTNVGSGA 58
```

POLYPEPTIDE-CALCITONIN 11 AND THE POLYNUCLEOTIDE ENCODING IT

This application is a 371 of PCT/CN00/00605, filed Dec. 18, 2000 which claims priority to Chinese application 99125679.4 filed Dec. 22, 1999.

FIELD OF INVENTION

The invention relates to the field of biotechnology. In particular, the invention relates to a novel polypeptide, calcitonin 11, and a polynucleotide sequence encoding the polypeptide. The invention also relates to the method for the preparation and use of the polynucleotide and polypeptide.

TECHNICAL BACKGROUND

Calcitonin, calcitonin Gene-related peptide (CGRP) and islet amyloid polypeptide (IAPP) have similarities in their structure. Calcitonin is a polypeptide hormone with 32 amino acid residues. By binding to the calcium ion, it can modulate the concentration of calcium ion in blood (Breimer, et al., 1988, Biochem. J. 255:377–390). CGRP is a polypeptide hormone with 39 amino acid residues. It can cause vasodilatation in different vessels (including coronary artery, blood vessel of brain, and the entire vascular system). IAPP is a polypeptide hormone with 37 amino acid residues. It can selectively inhibit glucose metabolism and glycogen synthesis which are induced by insulin (Nishi et al., 1990, J. Biol. Chem. 265: 4173–4176).

In almost all organisms, the three proteins share a conserved structural motif: C-[SAGDN]-[STN]-x (0,1)-[SA]-T-C-[VMA]-x (3)-[LYF]-x (3)-[LYF], and the two cysteines was bonded by a disulfide bond.

The conserved structural motif found in those three proteins is shown below:

```
          ***************
xCxxxxxCxxxxxxxxxxxxxxxxxxxxxxx——NH   (2)
|      |                              (Amide Group)
+------+
``` where * denotes conserved amino acid residues, C denotes the conserved cysteine. There are two conserved cysteines in the N-terminal, and the C-terminal of the protein was amidated. This conserved motif apparently plays a critical role to the physiological functions of calcitonin, CGRP and IAPP.

It is known that calcitonin is essential in the modulation of calcium concentration in the blood. It is used to treat infant hyperglycemia of unknown causes, and adult hypercalcimia caused by hyperparathyroidism. Calcitonin is also important in preventing loss of bone mass and decrease in bone density. Calcitonin deficiency will cause osteoporosis (BMJ, 1989; 298: 1215-6; Biochem J Oct. 15, 1988; 255: 377–90).

Research on the effect of CGRP on the brain and other tissues showed that CGRP can cause vasodilaiton, and it is an important regulator of blood flow and blood vessel tension. Furthermore, CGRP is important in the control of certain nervous system functions, actions of human cell and regulation of the endocrine system.

As discussed above, calcitonin plays an important role the regulation of many biological processes, which regulation is believed to require numerous proteins. It is, therefore, very important to identify additional proteins involved in the regulatory process. The isolation of the calcitonin 11 gene of the present invention enables the identification of its function under healthy and diseased conditions.

DISCLOSURE OF INVENTION

One objective of the invention is to provide an isolated novel polypeptide, i.e., a calcitonin 11, and fragments, analogues and derivatives thereof.

Another objective of the invention is to provide a polynucleotide encoding the polypeptide.

Another objective of the invention is to provide a recombinant vector containing a polynucleotide encoding a calcitonin 11.

Another objective of the invention is to provide a genetically engineered host cell containing a polynucleotide encoding a calcitonin 11.

Another objective of the invention is to provide a method for producing a calcitonin 11.

Another objective of the invention is to provide an antibody against a calcitonin 11 of the invention.

Another objective of the invention is to provide mimetics, antagonists, agonists, and inhibitors for the polypeptide of the calcitonin 11.

Another objective of the invention is to provide a method for the diagnosis and treatment of diseases associated with an abnormality of calcitonin 11.

The present invention relates to an isolated polypeptide, which is originated from human, and comprises a polypeptide having the amino acid sequence of SEQ ID NO: 2, or its conservative variants, or its active fragments, or its active derivatives and its analogues. Preferably, the polypeptide has the amino acid sequence of SEQ ID NO: 2.

The present invention also relates to an isolated polynucleotide, comprising a nucleotide sequence or its variant selected from the group consisting of (a) the polynucleotide encodeing a polypeptide comprising the amino acid sequence of SEQ ID NO: 2; and (b) a polynucleotide complementary to the polynucleotide (a); (c) a polynucleotide that shares at least 70% homology to the polynucleotide (a) or (b). Preferably, the nucleotide sequence is selected from the group consisting of (a) the sequence of position 211-501 in SEQ ID NO: 1; and (b) the sequence of position 1-1614 in SEQ ID NO: 1.

The invention also includes: a vector comprising a polynucleotide of the invention, especially an expression vector; a host cell genetically engineered with the vector via transformation, transduction or transfection; a method for the production of the inventive polypeptide through the process of host cell cultivation and expession product harvest.

The invention also relates to an antibody which specifically binds to the inventive polypeptide.

The invention also relates to a method for selecting compounds which could simulate, activate, antagonize, or inhibit the activity of the inventive polypeptide and the compounds obtained by the method.

The invention also relates to a method for in vitro diagnosis of diseases or disease susceptibility related with the abnormal expression of the inventive polypeptide. The method involves the detection of mutation in the polypeptide or its encoding polynucleotide sequence, or the determination of its quantity and/or biological activity in biological samples.

The invention also relates to pharmaceutical compositions which comprises the inventive polypeptide, its analogues, mimetics, agonists, antagonists, inhibitors, and a pharmaceutically acceptable carrier.

The invention also relates to applications of the inventive polypeptide and/or its polynucleotide for drug development to treat cancers, developmental diseases, immune diseases, or other diseases caused by abnormal expression of the inventive polypeptide.

Other aspects of the invention are apparent to the skilled in the art in view of the disclosure set forth hereinbelow.

The terms used in this specification and claims have the following meanings, unless otherwise noted.

"Nucleotide sequence" refers to oligonucleotide, nucleotide, or polynucleotide and parts of polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in the invention is related to the sequence of a natural protein, the amino acid sequence of the "peptide" or "protein" will not be limited to be identical to the sequence of that natural protein.

"Variant" of a protein or polynucleotide refers to the amino acid sequence or nucleotide sequence, respectively with one or more amino acids or one or more nucleotides changed. Such changes include deletion, insertion, and/or substitution of amino acids in the animo acid sequence, or of nucleotides in the polynucleotide sequence. In the case of polypeptides, these changes could be conservative and the substituted amino acid has similar structural or chemical characteristics as the original one, such as the substitution of Ile with Leu. Changes also could be not conservative, such as the substitution of Ala with Trp.

"Deletion" refers to the deletion of one or several amino acids in the amino acid sequence, or of one or several nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing number of the residues.

"Biological activity" refers to structural, regulatory or biochemical characteristics of a molecule. Similarly, the term "immunogenecity" refers to the ability of natural, recombinant, or synthetic proteins or other molecules to induce a specific immune reaction in an appropriate animal or cell, or to bind to a specific antibody.

"Agonist" refers to molecules which regulate, but generally enhance the activity of the inventive polypeptide by binding to and/or changing it. Agonists include proteins, nucleotides, carbohydrates or any other molecules which could bind to the inventive polypeptide.

"Antagonist" or "inhibitor" refers to molecules which inhibit or downregulate a biological activity or immunogenecity of the inventive polypeptide via binding to it. Antagonists or inhibitors include proteins, nucleotides, carbohydrates or any other molecules which bind to the inventive polypeptide.

"Regulation" refers to changes in the function of the inventive polypeptide, including up-regulation or down-regulation of the protein activity, changes in binding specifity, changes of any other biological characteristics, functional or immune characteristics.

"Substantially pure" refers to the condition of substantially free of other naturally related or associated proteins, lipids, saccharides, or other substances. One of ordinary skill in the art can purify the inventive polypeptide by standard protein purification techniques. Substantially pure polypeptide of the invention produces a single main band in a denaturing polyacrylamide gel. The purity of a polypeptide may also be analyzed by amino acid sequence analysis.

"Complementary" or "complementation" refers to the binding of polynucleotides by base pairing under approximate ion and temperature conditions. For instance, the sequence "C-T-G-A" could bind to its complementary sequence "G-A-C-T." The complementation between two single strand molecules could be partial or complete. Homology or sequence similarity between two single strands obviously influences the efficiency and strength of the formed hybrid.

"Homology" refers to the complementary degree, which may be partial or complete. "Partial homology" refers to a sequence being partially complementary to a target nucleotide. The sequence could at least partially inhibit the hybridization between a completely complementary sequence and the target nucleotide. Inhibition of hybridization could be assayed by hybridization (Southern blot or Northern blot) under less stringent conditions. Substantially complementary sequence or hybrid probe could compete with the completely complementary sequence and inhibit its hybridization with the target sequence under less stringent conditions. This does not mean that nonspecific binding is allowed under a less stringent condition, because specific or selective reaction is still required.

"Sequence Identity" refers to the percentage of sequence identity or similarity when two or several amino acid or nucleotide sequences are compared. Sequence identity may be determined by computer programs such as MEGALIGN (Lasergene Software Package, DNASTAR, Inc., Madison Wis.). MEGALIGN can compare two or several sequences using different methodologies such as the Cluster method (Higgins, D. G. and P. M. Sharp, 1988, Gene 73:237–244). Cluster method examines the distance between all pairs and arrange the sequences into clusters. Then the clusters are partitioned by pair or group. The sequence identity between two amino acid sequences such as sequence A and B can be calculated by the following equation:

$$\frac{\text{Number of paired identical residues between sequences } A \text{ and } B}{\text{Residue number of sequence } A - \text{number of gap residues in sequence } A - \text{number of gap residue in sequence } B} \times 100$$

Sequence identity between nucleotide sequences can also be determined by Cluster method or other well-known methods in the art such as the Jotun Hein method (Hein J., 1990, Methods in Emzymology 183:625–645)

"Similarity" refers to the degree of identity or conservative substitution degree of amino acid residues in corresponding sites of the amino acid sequences when compared to each other. Amino acids for conservative substitution are: negative charged amino acids including Asp and Glu; positively charged amino acids including Leu, Ile and Val; Gly and Ala; Asn and Gln; Ser and Thr; Phe and Tyr.

"Antisense" refers to the nucleotide sequences complementary to a specific DNA or RNA sequence. "Antisese strand" refers to the nucleotide strand complementary to the "sense strand."

"Derivative" refers to the inventive polypeptide or polynucleotide chemically or otherwise modified. This kind of modified chemical may be derived from replacement of the hydrogen atom with an alkyl, acyl, or amino group. The nucleotide derivative can encode peptide retaining the major biological characteristics of the natural molecule.

"Antibody" refers to the intact antibody or its fragments such as Fa, F (ab')2 and Fv, and it can specifically bind to antigenic epitopes of the inventive polypeptide.

"Humanized antibody" refers to an antibody which has its amino acid sequence in non-antigen binding region replaced to mimic human antibody and still retain the original binding activity.

The term "isolated" refers to the removal of a material out of its original environment (for instance, if it's naturally produced, original environment refers to its natural environment). For example, a naturally produced polynucleotide or a polypeptide in its original host organism means it has not been "isolated," while the separation of the polynucleotide or a polypeptide from its coexisting materials in natural system means it was "isolated." This polynucleotide may be a part of a vector, or a part of a compound. Since the vector or compound is not part of its natural environment, the polynucleotide or peptide is still "isolated."

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated calcitonin 11," means that calcitonin 11 does not essentially contain other proteins, lipids, carbohydrate or any other substances associated therewith in nature. The skilled in the art can purify calcitonin 11, by standard protein purification techniques. The purified polypeptide forms a single main band on a non-reducing PAGE gel. The purity of calcitonin 11 can also be analyzed by amino acid sequence analysis.

The invention provides a novel polypeptide—calcitonin 11, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of calcitonin 11. As used in the invention, the terms "fragment," "derivative" and "analogue" mean the polypeptide that essentially retains the same biological functions or activity of calcitonin 11 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, including a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 1614 bp, whose ORF (211–501) encodes a polypeptide of 96 amino acids, which has the characteristic sequence of the calcitonin family of proteins, and similar structures and functions as well.

The polynucleotide according to the invention may be in the forms of DNA or RNA. The forms of DNA include cDNA, genomic DNA, and synthetic DNA, etc., in single stranded or double stranded form. DNA may be a coding strand or a non-encoding strand. The coding sequence for mature polypeptide may be identical to the coding sequence shown in SEQ ID NO: 1, or is a degenerate sequence. As used herein, the term "degenerate sequence" means a sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence(s), the coding sequence for mature polypeptide (and optional additional encoding sequence) plus the non-coding sequence(s).

The term "polynucleotide encoding the polypeptide" includes polynucleotides encoding the polypeptide and polynucleotides comprising additional coding and/or non-coding sequences.

The invention further relates to variants of the above polynucleotides which encode a polypeptide having the same amino acid sequence of the invention, or a fragment, analogue and derivative of the polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and at a high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological functions and activities as the mature polypeptide of SEQ ID NO: 2.

The invention also relates to nucleic acid fragments hybridizing with the hereinabove sequence. As used in the present invention, the length of the "nucleic acid fragment" is at least 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding calcitonin 11.

The polypeptide and polynucleotide of the invention are preferably in the isolated form, preferably purified to be homogenous.

According to the invention, the specific nucleic acid sequence encoding calcitonin 11 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain double-stranded DNA.

Among the above methods, the isolation of genomic DNA is least frequently used. A commonly used method is the direct chemical synthesis of DNA sequence. A more frequently used method is the isolation of cDNA. Standard methods for isolating the cDNA of interest is to isolate mRNA from donor cells that highly express the gene, followed by reverse transcription of mRNA, and the establishment of plasmid or phage cDNA library. There are many established techniques for extracting mRNA and the kits are commercially available (e.g. Qiagene). Conventional method can be used to construct a cDNA library (Sambrook, et al., Molecular Cloning, A Laboratory Manual, Cold Spring Harbor Laboratory. New York, 1989). cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from a cDNA library. These methods include, but are not limited to, (1) DNA-DNA or DNA-RNA hybridization; (2) the appearance or loss of the function of the marker-gene; (3) the determination of the level of calcitonin 11 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleocides, preferably at least 30 nucleocides, more preferably at least 50 nucleocides, and still more preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. Labels for DNA probes include radioactive isotopes, fluoresceins or enzymes such as alkaline phosphatase.

In method (4), the detection of the protein products expressed by calcitonin 11 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (Random Amplification of cDNA Ends) is preferably used. The primers used in PCR can be selected according to the polynucleotide sequence information disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding calcitonin 11, and a method for producing the polypeptide of the invention by recombinant techniques.

In the present invention, the polynucleotide sequences encoding calcitonin 11 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125), the pMSXND expression vector for expression in mammalian cells (Lee and Nathans, J Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of calcitonin 11 and appropriate transcription/translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of *E. coli*; PL promoter of λ phage; eukaryotic promoters including CMV immediate early promoter, HSV thymidine kinase promoter, early and late SV40 promoter, LTRs of retroviruses, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for *E. coli*.

An ordinarily skilled in the art knows clearly how to select appropriate vectors, transcriptional regulatory elements, e.g., promoters, enhancers, and selective marker genes.

According to the invention, polynucleotide encoding calcitonin 11 or recombinant vector containing the polynucleotide can be transformed or transfected into host cells to construct genetically engineered host cells containing the polynucleotide or the recombinant vector. The term "host cell" means prokaryote, such as bacteria; or lower eukaryote, such as yeast; or higher eukaryotic, such as mammalian cells. Representative examples are bacterial cells, such as *E. coli, Streptomyces, Salmonella typhimurium*; fungal cells, such as yeast; plant cells; insect cells such as Drosophila S2 or Sf9; animal cells such as CHO, COS or Bowes melanoma.

Transformation of a host cell with a DNA sequence of the invention or a recombinant vector containing the DNA sequence may be carried out by conventional techniques as are well known to those skilled in the art. When the host is prokaryotic, such as *E. coli*, competent cells, which are capable of DNA uptake, can be prepared from cells harvested after exponential growth phase and subsequently treated by the CaCl2 method using procedures well known in the art. Alternatively, MgCl$_2$ can be used. Transformation can also be carried out by electroporation, if desired. When the host is an eukaryote, transfection methods as well as calcium phosphate precipitation may be used. Conventional mechanical procedures such as micro-injection, electroporation, or liposome-mediated transfection may also be used.

The recombinant calcitonin 11 can be expressed or produced by the conventional recombinant DNA technology (Science, 1984; 224:1431), using polynucleotide sequence of the invention. The steps generally include:

(1) transfecting or transforming the appropriate host cells with the polynucleotide (or variant) encoding calcitonin 11 of the invention or the recombinant expression vector containing the polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and a combination thereof.

BRIEF DESCRIPTION OF THE DRAWINGS

The following drawings are provided to illustrate the embodiment of the invention, not to limit the scope of invention defined by the claims.

EXAMPLES

Figures 1, 2:
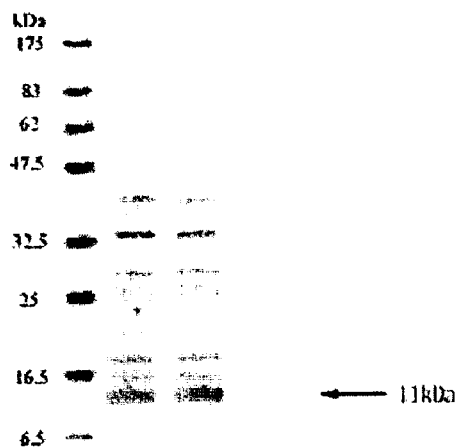
FIG. 1 is the homology comparison of the amino acid sequence of calcitonin 11 in this invention with the amino acid sequence of domain calcitonin family proteins in amino acid sequence from No. 12 to No. 95. "|", ":" and "." shows that the probability of appearance of different amino acid in the same position in two sequence is reduced in turn.
FIG. 2 shows an SDS-PAGE of the isolated calcitonin 11, which has a molecular weight of 11 kDa. The isolated protein band is marked with an arrow.

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Cloning of Calcitonin 11 Gene

Total RNA from a human embryonic brain was extracted by the one-step method with guanidinium isocyanate/phenol/chloroform. The poly (A) mRNA was isolated from the total RNA with Quik mRNA Isolation Kit (Qiegene). cDNA was prepared by reverse transcription with 2 µg poly (A) mRNA. The cDNA fragments were inserted into the polyclonal site of PBSK (+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 0259f12 was found to be a novel DNA sequence. The inserted cDNA sequence of clone 0259f12 was dual-directionally sequenced with a serial of synthesized primers. It was indicated that the full length cDNA contained in clone 0259f12 was 1614 bp (SEQ ID NO: 1) with a 291 bp ORF located in positions 211–501 which encodes a novel protein (SEQ ID NO: 2). This clone was named pBS-0259f12 and the encoded protein was named calcitonin 11.

Example 2

Domain Analysis of cDNA Clone

The DNA sequence of the calcitonin 11 gene and the amino acid sequence it encoded was analyzed with the profile scan program in GCG (Basic Local Alignment Search Tool) (Altschul, et al., J. Mol. Biol., 1990; 215:403-10), and domain analysis was carried out in databanks, such as Prosite. We found that calcitonin 11 is homologous to the characteristic motif of the calcitonin family proteins at the amino acid level, between positions No. 12 and No. 95 (probability is 0.2, the score is 11.36; threshold value is 11.32).

Example 3
Cloning Calcitonin 11 Gene by RT-PCR

Using total RNA extracted from a human embryonic brain as template, reverse transcription was carried out with oligo-dT primer to produce cDNAs. The cDNA was purified with a Qiagen Kit, and PCR was carried out with the following primers:

```
                                            (SEQ ID NO:3)
Primer 1: 5'-AATTATTTTCCTGCAGTGGTTTGC-3'

(SEQ ID NO:4)
Primer 2: 5'-GTGCTTTAACGAAGTTGTTTTATC-3'
```

Primer 1 is the forward sequence started from position 1 of 5' end of SEQ ID NO: 1.

Primer 2 is the reverse sequence of the 3' end of SEQ ID NO: 1.

The amplification condition was a 50 μl reaction system containing 50 mmol/L KCl, 10 mmol/L Tris-Cl (pH8.5), 1.5 mmol/L MgCl$_2$, 200 μmol/L dNTP, 10 pmol of each primer, 1U Taq DNA polymerase (Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–1614 bp of SEQ ID NO: 1.

Example 4
Northern Blotting of Expression of Calcitonin 11 Gene

Total RNA was extracted by one-step method (Anal. Biochem., 1987, 162, 156–159) with guanidinium isocyanate-phenol-chloroform. That is, homogenize the tissue using 4M guanidinium isocyanate-25 mM sodium citrate and 0.2M sodium acetate (pH 4.0), add 1 volume phenol and ⅕ volume chloroform-isoamyl alcohol (49:1), centrifuge after mixing. Take the acqueous phase, add 0.8 volume isopropyl alcohol, then centrifuge the mixture. Wash the RNA precipitation using 70% ethanol, dry, and dissolve it in water. 20 μg RNA was electrophoresed on the 1.2% agarose gel containing 20 mM 3-(N-morpholino) propane sulfonic acid (pH 7.0)-5 mM sodium acetate-1 mM EDTA-2.2 M formaldehyde. Then transfer it to a nitrocellulose filter. Prepare the $^{32}$P-labelled DNA probe with α-$^{32}$P dATP by the random primer method. The used DNA probe is the coding sequence (211bp-501 bp) of calcitonin 11 amplified by PCR as indicated in FIG. 1. The nitrocellulose filter with the transferred RNA was hybridized with the $^{32}$P-labelled DNA probe (2×10$^6$ cpm/ml) overnight in a buffer containing 50% formamide-25 mM KH$_2$PO$_4$ (Ph7.4)-5×Denhardt's solution and 200 μg/ml salmine and washed in 1×SSC-0.1% SDS, at 55° C., for 30 min. The filter was then analyzed and quantified using a phosphor imager.

Example 5
In Vitro Expression, Isolation and Purification of Recombinant Calcitonin 11

A pair of primers for specific amplification was designed based on SEQ ID NO: 1 and the encoding region in FIG. 1, the sequences are as follows:

```
                                            (SEQ ID No:5)
Primer 3: 5'-CCCCATATGGATTGATGTAGAGATTGGCCAATGA-3'

(SEQ ID No:6)
Primer 4: 5'-CATGGATCCTCACAAAGTTGCTGAGCCCACACAT-3'
```

These two primers contain a NdeI and BamHI cleavage site on the 5' end respectively. Within the sites are the coding sequences of the 5' and 3' end of the desired gene. NdeI and BamHI cleavage sites were corresponding to the selective cleavage sites on the expression vector pET-28b (+) (Novagen, Cat. No. 69865.3). PCR amplification was performed with the plasmid pBS-0259f12 containing the full-length target gene as a template. The PCR reaction was performed in a total volume of 50 μl containing 10 pg pBS-0259f12 plasmid, 10 pmol of Primer-3 and 10 pmol of Primer-4, and 1 μl of Advantage polymerase Mix (Clontech). The parameters of PCR were 94° C. 20 sec, 60° C. 30 sec, and 68° C. 2 min for 25 cycles. After digesting the amplification products and the plasmid pET-28 (+) by NdeI and BamHI, the large fragments were recovered and ligated with T4 ligase. The ligated product was transformed into *E. coli* DH5α cells with the calcium chloride method. After cultured overnight on an LB plate containing a final concentration of 30 μg/ml kanamycin, positive clones were selected using colony PCR and then sequenced. The positive clone (pET-0259f12) with the correct sequence was selected out and the recombinant plasmid thereof was transformed into BL21 (DE3)plySs (Novagen) using the calcium chloride method. In an LB liquid medium containing a final concentration of 30 μg/ml of kanamycin, the host bacteria BL21 (pET-0259f12) were cultured at 37° C. to the exponential growth phase, then IPTG were added with the final concentration of 1 mmol/L. The cells were cultured for another 5 hours, and then centrifuged to harvest the bacteria. After the bacteria were sonicated, the supernatant was collected by centrifugation. Then the purified desired protein-calcitonin 11 was obtained by a His.Bind Quick Cartridge (Novagen) affinity column with binding 6His-Tag. SDS-PAGE showed a single band at 11 kDa (FIG. 2). The band was transferred onto the PVDF membrane and the N-terminal amino acid was sequenced by Edams Hydrolysis, which shows that the first 15 amino acids on N-terminus were identical to those in SEQ ID NO: 2.

Example 6
Preparation of Antibody Against Calcitonin 11

The following specific calcitonin 11 polypeptide was synthesized by a polypeptide synthesizer (PE-ABI): NH$_2$-Met-Ser-Leu-Ala-Asn-Leu-Tyr-Ile-Asn-His-Trp-Gln-Gly-Glu-Leu-COOH (SEQ ID NO:7). The polypeptide was conjugated with hemocyanin and bovine serum albumin (BSA) respectively to form two composites (See Avrameas et al., Immunochemistry, 1969, 6:43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 μg/ml BSA-polypeptide composite by ELISA. Total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. Immunoprecipitation confirmed that the purified antibodies could specifically bind to calcitonin 11.

Example 7
Application of the Polynucleotide Fragments of the Invention as Hybridization Probes Oligonucleotides probes selected from the polynucleotide of the invention have many applications. The probe could be used to determine the existence of polynucleotide of the invention or its homologous polynucleotide sequences by hybridization with a genomic or cDNA library of normal or clinical tissues from various sources. The probes could be further used to determine whether polynucleotide of the invention or its homologous polynucleotide sequences are abnormally expressed in cells from normal or clinical tissues.

The purpose of the following example is to select suitable oligonucletide fragments from SEQ ID NO: 1 as hybird probes to apply in membrane hybridization to determine whether there is any polynucleotide of the invention or its homologous polynucleotide sequences in sample tissues. Membrane hybridization methods include dot blot, Southern blot, Northern blot, and replica hybridization. All methods follow nearly the same steps after the polynucleotide samples are immobilized on membranes. These steps are: membranes with immobilized samples are prehybridized in hybridization buffer not containing probes to block nonspecific binding sites of the membranes. Then the prehybridization buffer is replaced by hybridization buffer containing labeled probes and incubation is carried out at an appropriate temperature so probes hybridize with the target nucleotides. Free probes are washed off by a series of washing steps after the hybridization step. A high-stringency washing condition (relatively low salt concentration and high temperature) is applied in the example to reduce background and retain highly specific signals. Two types of probes are selected for the example: the first type of probes are oligonucleotides identical or annealed to SEQ ID NO:1; the second type probes are oligonucleotides partially identical or partially annealed to SEQ ID NO:1. Dot blot method is applied in the example for immobilization of the samples on membrane. The strongest specific signal produced by hybridization between first type probes and samples is obtained after relatively stringent membrane washing steps.

Selection of Probes

The principles below should be followed for the selection of oligonucleotide fragments from SEQ ID NO:1 as hybrid probes:

1. The optimal length of probes should be between eighteen and fifty nucleotides.
2. GC content should be between 30% and 70%, since nonspecific hybridization increases when GC content is more than 70%.
3. There should be no complementary regions within the probes themselves.
4. Probes meeting the requirements above could be initially selected for further computer-aided sequence analysis, which includes homology comparison between the initially selected probes and its source sequence region (SEQ ID NO: 1), other known genomic sequences and their complements. Generally, the initial selected probes should not be used when they share fifteen identical continuous base pairs, or 85% homology with non-target region.
5. Whether the initially selected probes should be chosen for final application depends upon further experimental confirmation.

The following two probes could be selected and synthesized after the analysis above:

Probe One belongs to the first type, which is completely identical or annealed to the gene fragments of SEQ ID NO: 1 (41 nucleotides):

5'-GGCAAGGTGAACTGGAATCTCAGCGATTGGCT ACAGCAGTT-3' (SEQ ID NO: 8)

Probe Two belongs to the second type which is a substituted or mutant sequence of a fragment of SEQ ID NO: 1 (41 nucleotides):

5'-GGATCGGTGAACTGGAAATCGAGCGATTGGCT AATCGAGTT-3' (SEQ ID NO: 9)

Other frequently used reagents not listed but involved in the following experimental steps and their preparation methods can be found, for example, in: DNA PROBES G. H. Keller; M. M. Manak; Stockton Press, 1989 (USA) or a more commonly used molecular cloning experimental handbook *Molecular Cloning* (J. Sambrook et al., Academic Press, 1998, 2nd Edition).

Sample Preparation:

1. DNA Extraction from Fresh or Frozen Tissues

Steps: 1) Place fresh or newly thawed tissue onto a dish on ice containing phosphate-buffered saline (PBS). Cut the tissue into small pieces with scissors or an operating knife. Tissues should be kept damp through the operation. 2) Mince the tissue by centrifugation at 2,000 g for 10 minutes. 3) Re-suspend the pellet (about 10 ml/g) with cold homogenating buffer (0.25 mol/l saccharose; 25 mmol/l Tris-HCl, pH7.5; 25 m mol/LnaCl; 25 mmol/L MgCl2) at 4° C., and homogenize the tissue suspension at full speed with an electronic homogenizer. 5) Centrifuge at 1,000 g for 10 minutes. 6) Re-suspend the cell pellet (1–5 ml per 0.1 g initial tissue sample), and centrifuge at 1,000 g for 10 minutes. 7) Re-suspend the pellet with lysis buffer (1–5 ml per 0.1 g initial tissue sample), and continue on to the phenol extraction step described below.

2. Phenol Extraction of DNA

Steps: 1) Wash cells with 1–10 ml cold PBS buffer and centrifuge at 1000 g for 10 minutes. 2) Re-suspend the precipitated cells with at least 100 µl cold cell lysis buffer (1×108 cells/ml). 3) Add SDS to a final concentration of 1%. Addition of SDS into the cell precipitation before cell re-suspension will cause the formation of large cell aggregates difficult to homogenize and reduce total yield. This is especially important when more than $10^7$ cells are used. 4) Incubate at 50° C. for an hour or shake gently overnight at 37° C. 5) Add an equal volume of phenol:chloroform:isoamyl alcohol (25:24:1) to the DNA solution to be purified in a microcentrifuge tube, and centrifuge for 10 minutes. If the two phases are not clearly separated, the solution should be recentrifuged. 6) Remove the acqueous phase to a new tube. 7) Add an equal volume of chloroform:isoamyl alcohol (24:1) and centrifuge for 10 minutes. 8) Remove the water phase containing DNA to a new tube and then purify DNA by ethanol precipitation.

3. DNA Purification by Ethanol Precipitation

Steps: 1) Add 1/10 vol of 2 mol/L sodium acetate and 2 vol of cold 100% ethanol into the DNA solution, mix and place at −20° C. for an hour or overnight. 2) Centrifuge for 10 minutes. 3) Carefully remove the ethanol. 4) Add 500 µl of cold 70% ethanol to wash the pellet and centrifuge for 5 minutes. 6) Carefully remove the ethanol and invert the tube on absorbent paper to remove remnant ethanol. Air dry for 10–15 minutes to evaporate the ethanol on the pellet surface. Do not dry the pellet completely since completely dry pellet is difficult to be dissolved again. 7) Re-suspend the DNA pellet with a small volume of TE or water. Spin at low speed or blow with a pipette, and add TE gradually and mix until DNA is completely dissolved. About 1 µl of DNA solution is obtained per 1~5×$10^6$ cells.

The following steps 8–13 are applied only when contamination must be removed, otherwise go directly to step 14. 8) Add RNase A into DNA solution to a final concentration of 100 μg/ml and incubate at 37° C. for 30 minutes. 9) Add SDS and protease K to the final concentration of 0.5% and 100 μg/ml individually, and incubate at 37° C. for 30 minutes. 10) Add an equal volume of phenol:chloroform:isoamyl alcohol (25:24:1), and centrifuge for 10 minutes. 11) Carefully remove the water phase and extract it with an equal volume of chloroform:isoamyl alcohol (24:1) and centrifuge for 10 minutes. 12) Carefully remove the water phase, and add 1/10 vol of 2 mol/L sodium acetate and 2.5 vol of cold 100% ethanol, then mix and place at −20° C. for an hour. 13) Wash the pellet with 70% ethanol and 100% ethanol, air dry and re-suspend DNA as same as the steps 3–6. 14) Determine the purity and production of DNA by A260 and A280 assay. 15) Separate DNA sample into several portions and store at −20° C.

Preparation of Sample Membrane

1) Take 4×2 pieces of nitrocellulose membrane (NC membrane) of desired size, and lightly mark out the sample dot sites and sample number with a pencil. Every probe needs two pieces of NC membrane, so then membranes could be washed under high stringency condition and moderate stringency condition individually in the following experimental steps.

2) Pipette 15 μl of samples and control individually, dot them on the membrane, and dry at room tempreture.

3) Place the membranes on filter paper soaked in 0.1 mol/LnaOH, 1.5 mol/L NaCl, leave for 5 minutes (twice), and allow to dry. Transfer the membranes on filter paper soaked in 0.5 mol/L Tris-HCl (pH7.0), 3 mol/L NaCl, leave for 5 minutes (twice), and allow to dry.

4) place the membranes between clean filter paper, packet with aluminum foil, and vacuum dry at 60–80° C. for 2 hours.

Labeling of Probes

1) Add 3 μl probe (0.1 OD/10 μl), 2 μl kinase buffer, 8–10 uCi γ-$^{32}$P-dATP+2U Kinase, and add water to the final volume of 20 μl.

2) Incubate at 37° C. for 2 hours.

3) Add 1/5 vol bromophenol blue indicator (BPB).

4) Load that sample on Sephadex G-50 column.

5) Collect the first peak before the elution of $^{32}$P-Probe (monitor the eluting process by Monitor).

6) Five drops each tube and collect for 10–15 tubes.

7) Measure the isotope amount with liquid scintillator.

8) Merged collection of the first peak is the prepared $^{32}$P-Probe (the second peak is free γ-$^{32}$P-dATP).

Prehybridization

Place the sample membranes in a plastic bag, add 3–10 mg prehybrid buffer (10×Denhardt's; 6×SSC, 0.1 mg/ml CT DNA (calf thymus gland DNA)), seal the bag, and shake on a 68° C. water bath for two hours hybridization.

Cut off a corner of the plastic bag, add in prepared probes, seal the bag, and shake on a 42° C. water bath overnight.

Membrane Washing

Membrane washing applying a high-stringency condition:

1) Take out the hybridized sample membranes

2) Wash the membranes with 2×SSC, 0.1% SDS at 40° C. for 15 minutes (twice).

3) Wash the membranes with 0.1×SSC, 0.1% SDS at 40° C. for 15 minutes (twice).

4) Wash the membranes with 0.1×SSC, 0.1% SDS at 55° C. for 30 minutes (twice), and dry at room temperature.

Membrane washing applying a low-stringency condition:

1) Take out the hybridized sample membranes.

2) Wash the membranes with 2×SSC, 0.1% SDS at 37° C. for 15 minutes (twice).

3) Wash the membranes with 0.1×SSC, 0.1% SDS at 37° C. for 15 minutes (twice).

4) Wash the membranes with 0.1×SSC, 0.1% SDS at 40° C. for 15 minutes (twice), and dry at room temperature.

X Ray Autoradiography:

X ray autoradiograph at −70° C. (autoradiograph time varies according to radioactivity of the hybrid spots).

Experimental Results:

In hybridization experiments carried out under low-stringency membrane washing condition, the radioactivity of all the above two probes hybridization spots show no obvious difference; while in hybridization experiments carried out under high-stringency membrane washing condition, radioactivity of the hybrid spot by probe one is obviously stronger than that of the other probes. So Probe One could be applied in qualitative and quantitative analyses of the existence and differential expression of the polynucleotide of the invention in different tissues.

Example 8

DNA Microarray

DNA-chip or DNA Microarray technology is now studied and developed in many laboratories and large pharmaceutical companies. The technology uses a large number of target genes that are arrayed on a glass or silicon slide with high density, then uses fluorescence detection and software to compare and analyze the data, so it can analyze a large amount scale of biology information quickly and effectively. The polynucleotide provided in this invention may be used as target DNA by DNA-chip technology to find new gene function, screen tissue-specific genes especially tumor related gene, and for disease (hereditary diseases etc.) diagnosis. The methods are known in the art (see e.g., DeRisi, et al. 1997, Science 278, 680–686; Helle, et al. 1997, PNAS 94:2150–2155.)

1. DNA Fixation 4000 cDNAs of various lengths were used as target DNA, including the polyneucleotide of this invention. cDNAs were amplified by PCR and purified, then adjusted to about 500 ng/μl. PCR products were printed on glass slide using Cartesian 7500 Robotics (Cartesian, USA), with a gap of 280 μm.

Printed arrays were hydrated, dried, UV cross-linked, rinsed and dried to fix the DNA on the glass slide. The details of the method have been reported in many documents. The step after fixation in this example is:

1) Incubate for 4 hr in a humid chamber;

2) Wash 1 min in 0.2% SDS;

3) Wash 2×1 min in ddH$_2$O;

4) Block for 5 min with NaBH$_4$;

5) Incubate in water at 95° C. for 2 min;

6) Wash 1 min in 0.2% SDS;

7) Wash twice with ddH$_2$O;

8) Air dry and store in the dark at 25° C.

2. Probe labeling

Total mRNA was extracted from normal liver cells and liver cancer cells by the one-step method, then purified using Oligotex mRNA Midi Kit (Qiagen). Following the reverse transcriptase step, mRNA from normal liver cells was labeled with Cy3dUTP (5-Amino-propargyl-2,-deoxyuridine 5,-triphate coupled to the Cy3 fluorescent dye, purchased from Amersham Phamacia Biotech Co.) and mRNA from liver cancer cells was labeled with Cy5dUTP (5-Amino-propargyl-2,-deoxyuridine 5,-triphate coupled to Cy5 fluorescent dye, purchased from Amersham Phamacia Biotech Co.). Then labeled probes were purified. (See Schena, et al., 1996, Proc.Natl. Acad.Sci., USA. 93:10614–10619; Schena, et al., 1995, Science. 270:467–480.).

3. Hybridization

Labeled probes from each tissue were mixed with the DNA-chip in UniHyb™ Hybridization Solution (TeleChem) for 16 hr. After washing with washing buffer (1×SSC, 0.2% SDS) at room temperature, Arrays were scaned using ScanArray 3000 (General Scanning Co., USA). The images were analyzed with Imagene (Biodiscovery Co., USA). The ratios of Cy3 to Cy5 were obtained. If the ratio is less than 0.5 or larger than 2, we can conclude the gene was expressed differently in two tissues.

The results showed that Cy3 signal=2005.25 (average of four experiments), Cy5 signal=1905.46 (average of four experiments), Cy3/Cy5=1.0281. So there is no obvious differential expression in the two tissues of the polynucleotide provided in this invention.

Industrial Applicability

The polypeptide of the invention and antagonists, agonists and inhibitors thereof can be directly used for the treatment of diseases, e.g., various malignant tumors or cancers, dermatitis, inflammation, adrenoprival disease and HIV infection and immune system diseases.

Calcitonin, CGRP and IAPP have a similar structural motif. Calcitonin is very important in the regulation of calcium concentration in the blood. The regulatory functions of calcitonin are closely related to physiological functions of parathormone, gastrin, pancreatin and glucagon. CGRP can cause vasodilatation in different vessels (including coronary artery, blood vessel of brain, and the entire vascular system), and it is an important factor in regulating blood flow and blood vessel tension. Furthermore, CGRP is also important in the modulation of some functions of nervous system, cellular behavior and endocrine system functions. IAPP can selectively inhibit glucose metabolism and glycogen synthesis induced by insulin.

Abnormal expression of calcitonin, CGRP, IAPP and the polypeptide of this invention may cause abnormal blood calcium level, cardiovascular system disorders, and abnormal blood sugar levels. These may further cause many diseases, for example: infant hyperglycemia, adult hypercalcimia, rachitis, osteomalacia, myeloma, parathyroid cyst, parathyrodioma, coronary heart disease, hypertension, diabetes, and diabetes and relted syndromes, aw well as certain hereditary diseases, hemopathy and immune diseases.

The polypeptide of the invention and its antagonist, agonist and inhibitors can be directly applied to treat some diseases, for example: infant hyperglycemia, adult hypercalcinemia, rachitis, osteomalacia, myeloma, parathyroid cyst, parathyrodioma, coronary heart disease, hypertension, diabetes, diease interrelated with diabetes, some hereditarydisease, hemopathy and immune diseases, etc.

The invention also provides methods for screening compounds so as to identify an agent which enhances calcitonin 11 activity (agonists) or decrease calcitonin 11 activity (antagonists). The agonists enhance the biological functions of calcitonin 11 such as inactivation of cell proliferation, while the antagonists prevent and alleviate disorders associated with excessive cell proliferation, such as various cancers. For example, in the presence of an agent, mammalian cells or membrane preparations expressing calcitonin 11 can be incubated with a labeled calcitonin 11 to determine the ability of the agent to enhance or repress the interaction.

Antagonists of calcitonin 11 include antibodies, compounds, receptor deletants and analogues. Antagonists of calcitonin 11 can bind to calcitonin 11 and eliminate or reduce its activity or inhibit the production, or bind to the active site of the polypeptide so that the polypeptide can not function biologically.

When screening for compounds as antagonists, calcitonin 11 may be added to a biological assay. It can be determined whether the compound is an antagonist or not by determining its effect on the interaction between calcitonin 11 and its receptor. Using the same method as that for screening compounds, receptor deletants and analogues acting as antagonists can be selected. Polypeptide molecules capable of binding to calcitonin 11 can be obtained by screening a polypeptide library comprising various combinations of amino acids bound onto a solid matrix. Calcitonin 11 is preferably labeled in the screening.

The invention further provides a method for producing antibodies using the polypeptide, fragments, derivatives, or analogues thereof, or cells comprising the polypeptide as an antigen. These antibodies may be polyclonal or monoclonal antibodies. The invention also provides antibodies against epitopes of calcitonin 11. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with calcitonin 11. Various adjuvants, including but are not limited to Freund's adjuvant, can be used to enhance the immunization. The techniques for producing calcitonin 11 monoclonal antibodies include, but are not limited to, the hybridoma technique (Kohler and Milstein, 1975, Nature 256:495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, 1985, PNAS 81:6851). Furthermore, techniques for producing a single-chain antibody (U.S. Pat. No. 4,946,778) are also useful for preparing single-chain antibodies against calcitonin 11.

The antibody against calcitonin 11 can be used in immunohistochemical method to detect the presence of calcitonin 11 in a biopsy specimen.

The monoclonal antibody specific to calcitonin 11 can be labeled by radioactive isotopes, and used in vivo to trace the location and distribution of calcitonin 11. This radioactively labeled antibody can be used in a non-invasive diagnostic method for the determination of tumor location and metastasis.

Antibodies can also be designed as an immunotoxin targeting a particular site in the body. For example, a monoclonal antibody having high affinity to calcitonin 11 can be covalently bound to bacterial or plant toxins, such as diphtheria toxin, ricin, ormosine. One common method is to attack the amino group on the antibody with sulfydryl cross-linking agents, such as SPDP, and bind the toxin onto the antibody by interchanging the disulfide bonds. This hybrid antibody can be used to kill calcitonin 11-positive cells.

The antibody of the invention is useful for the therapy or the prophylaxis of disorders related to the calcitonin 11. The appropriate amount of antibody can be administered to stimulate or block the production or activity of calcitonin 11.

The invention further provides diagnostic assays for quantitative and in situ measurement of calcitonin 11 level. Methods that can be used for these assays are well known in the art and include FISH assay and radioimmunoassay. The level of calcitonin 11 detected in the assay can be used to illustrate the role of calcitonin 11 in diseases and to determine diseases associated with calcitonin 11.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New calcitonin 11 polynucleotides also have many therapeutic applications. Gene therapy technology can be used in the treatment of abnormal cell proliferation, development or metabolism, which are caused by the loss of calcitonin 11 expression or the abnormal or non-active expression of calcitonin 11. Recombinant gene therapy vectors, such as viral vectors, can be designed to express mutated calcitonin 11 so as to inhibit the activity of endogenous calcitonin 11. For example, one form of mutated calcitonin 11 is a truncated calcitonin 11 whose signal transduction domain is deleted. Therefore, this mutated calcitonin 11 can bind to the downstream substrate without the activity of signal transduction. Thus, the recombinant gene therapy vectors can be used to cure diseases caused by abnormal expression or activity of calcitonin 11. The expression vectors derived from a virus, such as retrovirus, adenovirus, adeno-associated virus, herpes simplex virus, parvovirus, and so on, can be used to introduce the calcitonin 11 gene into the cells. The methods for constructing a recombinant virus vector harboring calcitonin 11 gene are described in the literature (Sambrook, et al. supra). In addition, the recombinant calcitonin 11 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozymes and oligonucleotides, including antisense RNA and DNA, which inhibit the translation of the calcitonin 11 mRNA. Ribozyme is an enzyme-like RNA molecule capable of specifically digesting certain RNA molecules. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding the RNA, wherein the DNA sequence is integrated into the vector and downstream of the RNA polymerase promoter. In order to increase its stability, a nucleic acid molecule can be modified in many manners, e.g., increasing the length of the two flanking sequences, and replacing the phosphodiester bond with the phosphothioester bond in the oligonucleotide.

Polynucleotides encoding calcitonin 11 can be used in the diagnosis of calcitonin 11 related diseases. Polynucleotides encoding calcitonin 11 can be used to detect whether calcitonin 11 is expressed or not, and whether the expression of calcitonin 11 is normal or abnormal in the case of diseases. For example, calcitonin 11 DNA sequences can be used in the hybridization with biopsy samples to determine the expression of calcitonin 11. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The calcitonin 11 specific primers can be used in RNA-polymerase chain reaction and in vitro amplification to detect transcripts of calcitonin 11.

Further, detection of mutations in calcitonin 11 gene is useful for the diagnosis of calcitonin 11-related diseases. Mutations of calcitonin 11 include site mutation, translocation, deletion, rearrangement and any other mutations compared with the wild-type calcitonin 11 DNA sequence. The conventional methods, such as Southern blotting, DNA sequencing, PCR and in situ blotting, can be used to detect a mutation. Moreover, mutations sometimes affect the expression of protein. Therefore, Northern blotting and Western blotting can be used to indirectly determine whether the gene is mutated or not.

Polypeptides of the present invention are also valuable for chromosome identification. The polypeptides can hybridize with a particular location on an individual human chromosome. There is a current need for identifying particular sites of gene on the chromosome. Few chromosomal markers based on actual sequence data (repeat polymorphism) are presently available for marking chromosomal location. The mapping of DNA to chromosomes according to the present invention is an important first step in correlating those sequences with genes associated with the disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in a similar manner. Other chromosome mapping strategies that can similarly be used to map to its chromosome include in situ hybridization, prescreening with labeled flow-sorted chromosomes and preselection by hybridization to construct chromosome specific-cDNA libraries.

A cDNA clone can be precisely mapped to a metaphase chromosomal spread in one step using fluorescence in situ hybridization (FISH). For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible at the chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effectiveness of the drug. These compositions can be used as drugs in disease treatment.

The invention also provides a pharmaceutical pack or kit comprising one or more containers filled with one or more of the ingredients of the pharmaceutical compositions of the invention. With such container (s) there may be a notice from a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. Calcitonin 11 is administered in an amount, which is effective for treating and/or prophylaxis of the specific indication. The amount of calcitonin 11 administrated to a patient will depend upon various factors, such as delivery methods, the subject's health, and the judgment of the skilled clinician.

We claim:

1. An isolated polypeptide having a calcitonin 11 activity and comprising an amino acid sequence of SEQ ID NO: 2.

2. An isolated polypeptide having a calcitonin 11 activity and comprising an amino acid sequence that is at least 95% identical to SEQ ID NO: 2.

3. A method for detecting a disease related to the polypeptide of claim 2, or for determining a susceptibility of a mammal thereto, said method comprising detecting the amount of expression of said polypeptide, or detecting the activity of said polypeptide.

4. A pharmaceutical composition comprising a polypeptide according to claim 2, and a pharmaceutically acceptable carrier.

* * * * *

SEQUENCE LISTING

```
<160> NUMBER OF SEQ ID NOS: 9

<210> SEQ ID NO 1
<211> LENGTH: 1614
<212> TYPE: DNA
<213> ORGANISM: Homo sapiens
<220> FEATURE:
<221> NAME/KEY: CDS
<222> LOCATION: (211)..(501)
<223> OTHER INFORMATION:

<400> SEQUENCE: 1
aattattttc ctgcagtggt ttgcaatccc tgtgcttccg ttggcctttc tttccttctt    60
ccaagatgtc tgccatctac cccatatcac gttctcacag ggcagcactc tcatcagaag   120
gaaggagaag aggagtttct ccttcacacg tcttgcattt tactgcagga aaataattcc   180
cagaattcgt cactgcagtc gttttcttag atg tca ttg gcc aat ctc tac atc   234
                                 Met Ser Leu Ala Asn Leu Tyr Ile
                                  1               5 aat cac tgg caa ggt gaa ctg gaa tct cag cga ttg gct aca gca gtt   282
Asn His Trp Gln Gly Glu Leu Glu Ser Gln Arg Leu Ala Thr Ala Val
     10                  15                  20 atg att cat ttg cag cat cag gca cat tgt tac ctg cac aaa agt agg   330
Met Ile His Leu Gln His Gln Ala His Cys Tyr Leu His Lys Ser Arg
 25                  30                  35                  40 att tac tta aac tgg agg aag cag aaa atg cac tcc agt gtt gtt act   378
Ile Tyr Leu Asn Trp Arg Lys Gln Lys Met His Ser Ser Val Val Thr
                 45                  50                  55 caa tgg agt ctg cta caa aag gaa ttc aca ggg gtc cac tct gtt tgt   426
Gln Trp Ser Leu Leu Gln Lys Glu Phe Thr Gly Val His Ser Val Cys
             60                  65                  70 cag ggt gct ggt ttc ctg tca tta gtt ttc att act ctc ttt cat cct   474
Gln Gly Ala Gly Phe Leu Ser Leu Val Phe Ile Thr Leu Phe His Pro
         75                  80                  85 aca tgt gtg ggc tca gca act ttg tga attctggttt gtggaatttg          521
Thr Cys Val Gly Ser Ala Thr Leu
     90                  95 acacagatga tttctctgcc aacattgaat ctcacaggtc acatcttcca tcctaaccta   581
tatcctaact tttctaccta tcttggcatt gtctttgtat tttgccttgt gtaatttgga   641
ctgcactgga tatagtcttt ggtcatatcc cctcagcatt aggtgtgggc agcaggcatg   701
gggcatcgtg cattagtaac cagctcagcc cacagatgct gtccatgagc ttcctgtccc   761 ctaccctcc ccaaagaagg gcatcagcca gttactccca acagtagggt cactcttctc   821
agagaactat tgggattact tacatcgctc ggttgttacg cacactacac aacagggaaa   881
```

-continued

```
cttgttcatt cctccgtccc aaggtttgtc aatctagagt agactgagtg ttcttctgag    941
cttgcaattc acattattgg ctggattctt ctggggacat ggtcagagga gctcactatg   1001
gaatctgtgc attaaccact cctgatccta taggctgtat ttaccagctt gttctagcat   1061
cagcacaggt tatggtgata gttgtacagt gaccatatcc aattatcaac atttacctct   1121
ccagcatctg caccaacaga tggacaaata acaactaag agagaaataa aatgatcctg    1181
ggggcctgtt gtttccctga actatctacc agttgaggga gattgtatgt tcataggtg   1241 ggagattcca aagcccacct ttctgagcac tcataaaata tttgattaca aagggatctt   1301
tgtgcttgag tggtagatgt tggtttgggg gctgattaac gagcttagtt agaaaactac   1361
taggtagcca aatgcatgac tgccagattc tgttctgtgg attcaaatac tgatctgcaa   1421
tatggcaatg tgactctata gtcagcatac taggaagggt ggttagggct ggtgaagcac   1481
tggtatggac ttaggttcag atcccacttc taaatgctcc ttagtgtctc aaagctttac   1541
tttacctata cgtaaaataa gaatagcttt ctcataggat tggtgactgg ataaaacaac   1601
ttcgttaaag cac                                                      1614
```

<210> SEQ ID NO 2
<211> LENGTH: 96
<212> TYPE: PRT
<213> ORGANISM: Homo sapiens

<400> SEQUENCE: 2

```
Met Ser Leu Ala Asn Leu Tyr Ile Asn His Trp Gln Gly Glu Leu Glu
 1               5                  10                  15

Ser Gln Arg Leu Ala Thr Ala Val Met Ile His Leu Gln His Gln Ala
            20                  25                  30

His Cys Tyr Leu His Lys Ser Arg Ile Tyr Leu Asn Trp Arg Lys Gln
        35                  40                  45

Lys Met His Ser Ser Val Val Thr Gln Trp Ser Leu Leu Gln Lys Glu
    50                  55                  60

Phe Thr Gly Val His Ser Val Cys Gln Gly Ala Gly Phe Leu Ser Leu
65                  70                  75                  80

Val Phe Ile Thr Leu Phe His Pro Thr Cys Val Gly Ser Ala Thr Leu
                85                  90                  95
```

<210> SEQ ID NO 3
<211> LENGTH: 24
<212> TYPE: DNA
<213> ORGANISM: Artificial
<220> FEATURE:
<223> OTHER INFORMATION: oligonucleotide primer

<400> SEQUENCE: 3

```
aattattttc ctgcagtggt ttgc                                            24
```

<210> SEQ ID NO 4
<211> LENGTH: 24
<212> TYPE: DNA
<213> ORGANISM: Artificial
<220> FEATURE:
<223> OTHER INFORMATION: oligonucleotide primer

<400> SEQUENCE: 4

```
gtgctttaac gaagttgttt tatc                                            24
```

<210> SEQ ID NO 5

```
<211> LENGTH: 34
<212> TYPE: DNA
<213> ORGANISM: Artificial
<220> FEATURE:
<223> OTHER INFORMATION: oligonucleotide primer

<400> SEQUENCE: 5
ccccatatgg attgatgtag agattggcca atga                              34

<210> SEQ ID NO 6
<211> LENGTH: 34
<212> TYPE: DNA
<213> ORGANISM: Artificial
<220> FEATURE:
<223> OTHER INFORMATION: oligonucleotide primer

<400> SEQUENCE: 6
catggatcct cacaaagttg ctgagcccac acat                              34

<210> SEQ ID NO 7
<211> LENGTH: 15
<212> TYPE: PRT
<213> ORGANISM: Artificial
<220> FEATURE:
<223> OTHER INFORMATION: portion of SEQ ID NO:2

<400> SEQUENCE: 7

Met Ser Leu Ala Asn Leu Tyr Ile Asn His Trp Gln Gly Glu Leu
1               5                   10                  15

<210> SEQ ID NO 8
<211> LENGTH: 41
<212> TYPE: DNA
<213> ORGANISM: Artificial
<220> FEATURE:
<223> OTHER INFORMATION: oligonucleotide primer

<400> SEQUENCE: 8
ggcaaggtga actggaatct cagcgattgg ctacagcagt t                      41

<210> SEQ ID NO 9
<211> LENGTH: 41
<212> TYPE: DNA
<213> ORGANISM: Artificial
<220> FEATURE:
<223> OTHER INFORMATION: oligonucleotide primer

<400> SEQUENCE: 9
ggatcggtga actggaaatc gagcgattgg ctaatcgagt t                      41
```